(12) United States Patent
Lee et al.

(10) Patent No.: US 11,701,327 B2
(45) Date of Patent: Jul. 18, 2023

(54) PHARMACEUTICAL COMPOSITIONS AND USES THEREOF

(71) Applicant: I-SHOU UNIVERSITY, Kaohsiung (TW)

(72) Inventors: Mei-Hwa Lee, Kaohsiung (TW); Hung-Yin Lin, Kaohsiung (TW)

(73) Assignee: I-SHOU UNIVERSITY, Kaohsiung (TW)

( * ) Notice: Subject to any disclaimer, the term of this patent is extended or adjusted under 35 U.S.C. 154(b) by 164 days.

(21) Appl. No.: 17/230,979

(22) Filed: Apr. 14, 2021

(65) Prior Publication Data

US 2021/0228486 A1 Jul. 29, 2021

Related U.S. Application Data

(62) Division of application No. 16/686,210, filed on Nov. 18, 2019, now Pat. No. 11,007,149.

(51) Int. Cl.
| | |
|---|---|
| *A61K 9/107* | (2006.01) |
| *A61K 31/404* | (2006.01) |
| *A61K 31/12* | (2006.01) |
| *A61K 47/24* | (2006.01) |
| *A61K 47/26* | (2006.01) |
| *A61K 47/44* | (2017.01) |
| *A61P 35/00* | (2006.01) |

(52) U.S. Cl.
CPC ............ *A61K 9/1075* (2013.01); *A61K 31/12* (2013.01); *A61K 31/404* (2013.01); *A61K 47/24* (2013.01); *A61K 47/26* (2013.01); *A61K 47/44* (2013.01); *A61P 35/00* (2018.01)

(58) Field of Classification Search
CPC .... A61K 9/1075; A61K 31/12; A61K 31/404; A61K 47/24; A61K 47/26; A61K 47/44; A61P 35/00
See application file for complete search history.

(56) References Cited

PUBLICATIONS

Cancer Research UK, Controlling symptoms of brain tumours, 2019, Cancer Research UK, https://www.cancerresearchuk.org/about-cancer/brain-tumours/treatment/controlling-symptoms (Year: 2019).*

* cited by examiner

*Primary Examiner* — Bethany P Barham
*Assistant Examiner* — Ayaan A Alam

(57) ABSTRACT

Provided herein is a pharmaceutical composition for treating cancers. The pharmaceutical composition includes an oil-in-water (o/w) microemulsion, and an active pharmaceutical ingredient dissolved therein. The o/w microemulsion is comprised of an aqueous solution, an oil, and a surfactant, and is about 5-250 nm in diameter. Also provided herein are methods for treating cancers by use of the present pharmaceutical composition.

7 Claims, 10 Drawing Sheets

A

B

A

B

PHARMACEUTICAL COMPOSITIONS AND USES THEREOF

BACKGROUND OF THE INVENTION

1. Field of the Invention

The present disclosure in general relates to the field of disease treatment. More particularly, the present disclosure relates to a pharmaceutical formulation and uses thereof in the treatment of cancers.

2. Description of Related Art

In the early stage of drug development, a major challenge has been finding a way to efficiently deliver active pharmaceutical ingredients (API) of low water solubility into patients. In response to such challenge, microemulsion type of formulations are developed, in which the API's water solubility is increased, which in terms leads to enhanced bioavailability of such API in patients. Nevertheless, formulations of such sort increase the API's bioavailability at the expense of normal cells and/or tissues, as API of such sort (e.g., anti-cancer drugs inhibiting cell proliferation) are often toxic, thus, increasing the API's water solubility would inevitably result in more toxic drugs being absorbed by the normal cells and/or tissues, which leads to more damages to the normal cells and/or tissues.

In view of the foregoing, there exists in the related art a need for an improved drug delivery system, in which not only does the bioavailability of the API of low water solubility in patients increase, but also the delivery of the API to target cells (e.g., cancer cells) is enhanced, so that side effects caused by damage to the normal cells are reduced.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a pharmaceutical composition comprising an oil-in-water (o/w) microemulsion and an API dissolved in the o/w microemulsion; wherein the o/w microemulsion comprises an aqueous solution, an oil, and a surfactant, which are respectively present in a ratio of about 30-85:1:2-17 by weight in the o/w microemulsion; and the o/w microemulsion is about 5-250 nm in diameter.

According to some preferred embodiments of the present disclosure, in the o/w microemulsion, the solution, the oil, and the surfactant are respectively present in a ratio of about 40-80:1:3-8.

In some embodiments of the present disclosure, the aqueous solution is water or a buffered solution.

In certain embodiments of the present disclosure, the oil is almond oil, canola oil, castor oil, corn oil, cottonseed oil, olive oil, safflower oil, sesame oil, soybean oil, isopropyl myristate, isopropyl palmitate, isopropyl stearate, ethyl oleate, myristic alcohol, oleyl alcohol, myristic acid, oleyl acid, palmitic acid, triglycerides, diglycerides, monoglycerides, or a combination thereof.

In some embodiments of the present disclosure, the surfactant in the o/w microemulsion is consisted of a first and a second emulsifiers in a ratio from about 0.1:1 to 50:1 by weight.

In still some embodiments of the present disclosure, the first emulsifier is egg lecithin, glycerophosphocholine, hydrogenated phosphatidyl choline, hydrogenated phospholipids, hydrogenated soybean lecithin, phospholipids, sodium lauryl sulphate, soybean lecithin, or soybean lysolecithin.

In yet some embodiments of the present disclosure, the second emulsifier is caprylocaproyl polyoxylglyceride, lauroyl polyoxylglyceride, oleoyl polyoxylglyceride, pegylated hydroxystearate, pegylated stearate, polyoxyethylene castor oil, polyoxyethylene cetostearyl ether, polyoxyethylene cetyl stearyl ether, polyoxyethylene dioleate, polyoxyethylene glycol cetyl ether, polyethylene glycol stearyl ether, polyoxyethylene hydrogenated castor oil, polyoxyethylene isostearyl ether, polyethylene laurate, polyoxyethylene monocetyl ether, polyoxyethylene oleate, polyoxyethylene sorbitan, or sorbitan. In one specific embodiment of the present disclosure, the first emulsifier is soybean lecithin, and the second emulsifier is polyoxyethylene sorbitan.

In some embodiments of the present disclosure, the API is an anti-cancer drug. Exemplary anti-cancer drug used herein includes, but is not limited to, altretamine, aminoglutethimide, amsacrin, anastrozole, anthracycline, antiestrogen, bexaroten, bortezomib, busulfan, camptothecin, capecitabine, carboplatin, chlorambucil, cisplatin, cladribine, clofarabine, curcumin, dacarbazine, dactinomycin, dexamethasone, docetaxel, doxorubicin, estrone, estradiol, estriol, etoposide, exemestane, fludarabine, fluorouracil, formestane, foxuridine, gemcitabine, glucocorticoid, idarubicin, indirubin, imatinib, irinotecan, ixabepilone, letrozole, leuprolide, lomustine, mechlorethamine, melphalan, mercaptopurine, methotrexate, mitomycin, mitoxantrone, nintedanib, oxaliplatin, paclitaxel, plicamycin, prednisone, procarbazine, progesterone, tamoxifen, temozolomide, teniposide, testolactone, testosterone, thioguanine, treosulfan, tretinoin, triptorelin, trofosfamide, vinblastine, and vindesine. In one specific embodiment of the present disclosure, the anti-cancer drug is indirubin. In another specific embodiment of the present disclosure, the anti-cancer drug is curcumin.

Another aspect of the present disclosure pertains to a method for treating a cancer in a subject. The method comprises the step of administering to the subject in need thereof an effective amount of the present pharmaceutical composition.

In some embodiments of the present disclosure, the pharmaceutical composition may be given to the subject via any suitable route, for example, via oral, intratumoral, intracranial, intraspinal, intrathecal, intramedullar, intracerebral, intracerebroventricular, intravenous, intraarterial, intracardial, intracutaneous, subcutaneous, transdermal, intraperitoneal, or intramuscular administration.

Examples of cancers treatable by the present pharmaceutical composition and/or method include, but are not limited to, bladder cancer, biliary cancer, bone cancer, brain tumor, breast cancer, cervical cancer, colorectal cancer, dysgerminoma, esophageal cancer, epidermal cancer, gastric cancer, gastrointestinal stromal tumor (GIST), glioma, non-Hodgkin's lymphoma, head and neck cancer, intestinal cancer, Kaposi's sarcoma, liver cancer, lung cancer, lymphoma, lymphoid leukemia, melanoma, myeloid leukemia, nasopharyngeal cancer, oral cancer, ovary cancer, pancreatic cancer, prostate cancer, retinoblastoma, renal cell carcinoma, sarcoma, seminoma, skin cancer, spleen cancer, squamous cell carcinoma, teratoma, teratocarcinoma, thyroid cancer, and thyroid follicular cancer. In one specific example of the present disclosure, the cancer is the lung cancer.

In one preferred embodiment of the present disclosure, the subject is a human.

Many of the attendant features and advantages of the present disclosure will becomes better understood with reference to the following detailed description considered in connection with the accompanying drawings.

BRIEF DESCRIPTION OF THE DRAWINGS

These and other features, aspects and advantages of the present invention will become better understood with reference to the following description, appended claims and the accompanying drawings, where:

DESCRIPTION

Figure 1A:
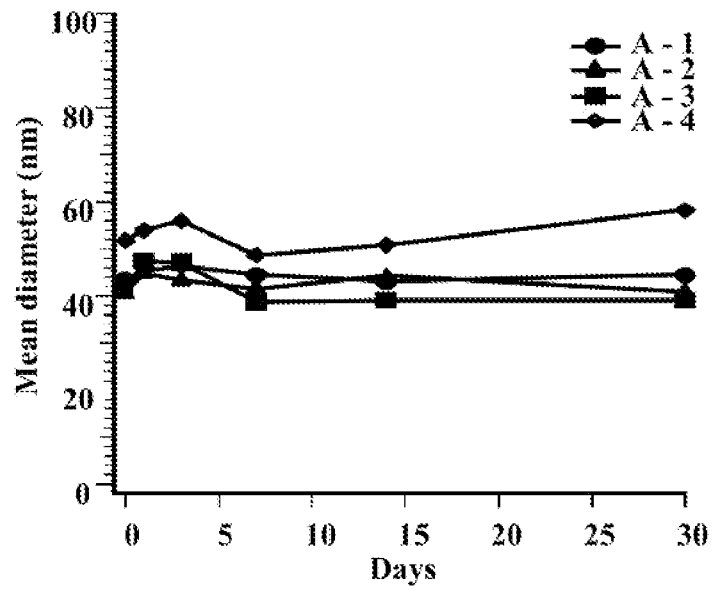
FIGS. 1A-1C depict the results of the mean diameter of the formulations A-1 to A-4 (FIG. 1A), B-1 to B-4 (FIG. 1B), and C-1 to C-4 (FIG. 1C) in accordance with one embodiment of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a," "an," and "the" include the plural reference unless the context clearly dictates otherwise. Also, as used herein and in the claims, the terms "at least one" and "one or more" have the same meaning and include one, two, three, or more. The practice of the present invention will employ, unless otherwise indicated, conventional techniques of molecular biology, microbiology, recombinant DNA, and immunology, which are within the skill of the art. Such techniques are explained fully in the literature.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, an "oil-in-water microemulsion" refers to a microemulsion comprised of at least 50 percent (w/w) aqueous solution, at least one organic chemical that is normally substantially immiscible in the aqueous solution (e.g., an oil), and at least one surfactant. The oil is the dispersed phase which is dispersed as droplets in the continuous phase (i.e., the aqueous solution), wherein the droplets typically have a mean diameter of less than about 300 nm, e.g., about 5-250 nm. A microemulsion typically has a clear or translucent appearance on visual inspection by virtue of the droplets too small to scatter light of visible wavelengths. A microemulsion generally has viscosities lower than liquid crystals, e.g., about 10-400 mPa·s.

The term "an active pharmaceutical ingredient (API)" as used herein refers to the ingredient in a pharmaceutical drug that is biologically active, and in general has a low water solubility or substantially water immiscible. The water solubility of the API in the present disclosure is less than or equal to 10 mg/ml; more preferably, less than or equal to 1 mg/ml; even preferably, less than or equal to $10^{-1}$ mg/ml; even more preferably, less than or equal to $10^{-2}$ mg/ml; most preferably, less than or equal to $10^{-3}$ mg/ml.

The terms "treatment" and "treating" as used herein may refer to a curative or palliative measure. In particular, the term "treating" as used herein refers to the application or administration of the present pharmaceutical composition or kit comprising the same to a subject, who has a cancer, a symptom associated with the cancer, a disease or disorder secondary to the cancer, with the purpose to partially or completely alleviate, ameliorate, relieve, delay onset of, inhibit progression of, reduce severity of, and/or reduce incidence of one or more symptoms or features of the cancer.

The terms "cancer" and "tumor" are used alternatively in the present disclosure and preferably refer to the physiological condition in mammals and especially in humans that is typically characterized by un-regulated cell growth. Cancers in this respect include metastases cancers, and/or drug-resistant cancers. Exemplary cancers or tumors treatable with the present disclosure include, but are not limited to, breast cancer, lung cancer, colon cancer, colorectal cancer, spleen cancer, kidney cancer, liver cancer, bladder cancer, head and neck cancer, ovary cancer, prostate cancer, brain tumor, pancreas cancer, skin cancer, bone tumor, leukemia, thymus cancer, uterus cancer, testicles cancer, and cervix cancer.

The term "subject" or "patient" refers to an animal including human species that is treatable with the compositions and/or methods of the present disclosure. The term "subject" or "patient" intended to refer to both the male and female gender unless one gender is specifically indicated. Accordingly, the term "subject" or "patient" comprises any mammal which may benefit from treatment of cancer. Examples of a "subject" or "patient" treatable with the present compositions and/or methods include, but are not limited to, a human, rat, mouse, guinea pig, monkey, pig, goat, cow, horse, dog, cat, bird and fowl. In an exemplary embodiment, the subject is a human.

The terms "administered," "administering" or "administration" are used interchangeably herein to refer to directly give a pharmaceutical composition of the present disclosure to a subject.

The term "an effective amount" as used herein refers to an amount effective, at dosages, and for periods of time necessary, to achieve the desired therapeutically desired result with respect to the treatment of cancers.

II. Description of the Invention

The present disclosure is based, at least in part, on the discovery that the present o/w microemulsion, which is formulated by an aqueous solution, an oil, and a surfactant in a specific ratio, may increase the solubility of an API that is substantially water immiscible, and specifically deliver the API to target cells without damaging non-target cells; in this fashion, the present o/w microemulsion may improve drug availability while reducing side effects of drugs at the same time.

1. The Present Pharmaceutical Composition

This present disclosure encompasses a pharmaceutical composition comprising an oil-in-water (o/w) microemulsion and an active pharmaceutical ingredient (API) dissolved therein; wherein the o/w microemulsion comprises an aqueous solution, an oil, and a surfactant, which are respectively present in a ratio of about 30-85:1:2-17 by weight in the o/w microemulsion; and the o/w microemulsion is about 5-250 nm in diameter.

Examples of the aqueous solution suitable for formulating the o/w microemulsion include water and a buffered solution. Said water may be any type of purified water, such as deionized water, distilled water, demineralized water, or pure water; or may be water containing minerals or slats, such as tap water, mineral water. Said buffered solution may be any type of a buffered solution, such as a phosphate buffered solution (PBS). Nevertheless, the material for the aqueous solution of the o/w microemulsion described herein is not limited thereto. In one specific example, the aqueous solution for formulating the o/w microemulsion is deionized water.

Examples of oil suitable for formulating the o/w microemulsion include almond oil, beech nut oil, bitter gourd oil, bottle gourd oil, brazil nut oil, buffalo gourd oil, butter, butternut squash seed oil, canola oil, cashew oil, castor oil, coconut oil, corn oil, cottonseed oil, egusi seed oil, grapefruit seed oil, hazelnut oil, lard, lemon oil, macadamia oil, mongongo nut oil, olive oil, orange oil, palm oil, palm kernel oil, peanut oil, pecan oil, pine nut oil, pistachio oil, pumpkin seed oil, rapeseed oil, safflower oil, sesame oil, soybean oil, sunflower oil, walnut oil, watermelon seed oil, diglycerides, ethyl oleate, isopropyl myristate, isopropyl palmitate, isopropyl stearate, monoglycerides, myristic acid, myristic alcohol, oleyl acid, oleyl alcohol, palmitic acid, triglycerides, and etc. In some embodiments, a combination of aforementioned oils is used to formulate the o/w microemulsion. However, the material for the oil of the o/w microemulsion described herein is not limited thereto; any edible oil, including vegetable oil or animal oil, may be used in the present disclosure. Therefore, the o/w microemulsion formulated by edible oil is encompassed within the scope of the present disclosure. In one specific example, olive oil is chosen for formulating the present o/w microemulsion.

According to some embodiments of the present disclosure, a first and a second emulsifiers are combined to act as the surfactant for formulating the present o/w microemulsion. Exemplary first emulsifier includes, but is not limited to, egg lecithin, glycerophosphocholine, hydrogenated phosphatidyl choline, hydrogenated phospholipids, hydrogenated soybean lecithin, phospholipids, sodium lauryl sulphate, soybean lecithin, and soybean lysolecithin. Exemplary second emulsifier includes, but is not limited to, caprylocaproyl polyoxylglyceride, lauroyl polyoxylglyceride, oleoyl polyoxylglyceride, pegylated hydroxystearate, pegylated stearate, polyoxyethylene castor oil, polyoxyethylene cetostearyl ether, polyoxyethylene cetyl stearyl ether, polyoxyethylene dioleate, polyoxyethylene glycol cetyl ether, polyethylene glycol stearyl ether, polyoxyethylene hydrogenated castor oil, polyoxyethylene isostearyl ether, polyethylene laurate, polyoxyethylene monocetyl ether, polyoxyethylene oleate, polyoxyethylene sorbitan, and sorbitan.

According to embodiments of the present disclosure, the first and the second emulsifiers are combined in a ratio from about 0.1:1 to 50:1 by weight to form the surfactant for formulating the present o/w microemulsion. For example, the first and the second emulsifiers are combined in the ratio of 0.1:1, 0.15:1, 0.2:1, 0.25:1, 0.3:1, 0.35:1, 0.4:1, 0.45:1, 0.5:1, 0.55:1, 0.6:1, 0.65:1, 0.7:1, 0.75:1, 0.8:1, 0.85:1, 0.9:1, 0.95:1, 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, 10.5:1, 11:1, 11.5:1, 12:1, 12.5:1, 13:1, 13.5:1, 14:1, 14.5:1, 15:1, 15.5:1, 16:1, 16.5:1, 17:1, 17.5:1, 18:1, 18.5:1, 19:1, 19.5:1, 20:1, 20.5:1, 21:1, 21.5:1, 22:1, 22.5:1, 23:1, 23.5:1, 24:1, 24.5:1, 25:1, 25.5:1, 26:1, 26.5:1, 27:1, 27.5:1, 28:1, 28.5:1, 29:1, 29.5:1, 30:1, 30.5:1, 31:1, 31.5:1, 32:1, 32.5:1, 33:1, 33.5:1, 34:1, 34.5:1, 35:1, 35.5:1, 36:1, 36.5:1, 37:1, 37.5:1, 38:1, 38.5:1, 39:1, 39.5:1, 40:1, 40.5:1, 41:1, 41.5:1, 42:1, 42.5:1, 43:1, 43.5:1, 44:1, 44.5:1, 45:1, 45.5:1, 46:1, 46.5:1, 47:1, 47.5:1, 48:1, 48.5:1, 49:1, 49.5:1, or 50:1; preferably, 0.4:1 to 40:1 by weight; more preferably, 0.55:1 to 37:1 by weight. In some embodiments, the first and the second emulsifiers are combined in the ratio of about 0.4:1 to 1:1 by weight, such as 0.4:1, 0.45:1, 0.5:1, 0.55:1, 0.6:1, 0.65:1, 0.7:1, 0.75:1, 0.8:1, 0.85:1, 0.9:1, 0.95:1, or 1:1. In other embodiments, the first and the second emulsifiers are combined in the ratio of about 0.4:1 to 0.75:1 by weight, such as 0.4:1, 0.5:1, 0.6:1, and 0.75:1. In still other embodiments, the first and the second emulsifiers are combined in the ratio of about 0.55:1 to 1:1 by weight, such as 0.55:1, 0.65:1, 0.8:1, and 1:1. In yet still other embodiments, the first and the second emulsifiers are combined in the ratio of about 11.5:1 to 37:1 by weight, such as 11.5:1, 12.5:1, 34.5:1, and 37:1.

According to one specific embodiment, the first and second emulsifiers are respectively soybean lecithin and polyoxyethylene sorbitan, which are combined in the ratio of 0.5-1:1 to serve as the surfactant for formulating the present o/w microemulsion.

According to embodiments of the present disclosure, the present o/w microemulsion is formulated by use of the aforementioned aqueous solution, oil, and surfactant in a weight ratio from about 30-85:1:2-17, such as 30:1:2-17, 30.5:1:2-17, 31:1:2-17, 31.5:1:2-17, 32:1:2-17, 32.5:1:2-17, 33:1:2-17, 33.5:1:2-17, 34:1:2-17, 34.5:1:2-17, 35:1:2-17, 35.5:1:2-17, 36:1:2-17, 36.5:1:2-17, 37:1:2-17, 37.5:1:2-17, 38:1:2-17, 38.5:1:2-17, 39:1:2-17, 39.5:1:2-17, 40:1:2-17, 40.5:1:2-17, 41:1:2-17, 41.5:1:2-17, 42:1:2-17, 42.5:1:2-17, 43:1:2-17, 43.5:1:2-17, 44:1:2-17, 44.5:1:2-17, 45:1:2-17, 45.5:1:2-17, 46:1:2-17, 46.5:1:2-17, 47:1:2-17, 47.5:1:2-17, 48:1:2-17, 48.5:1:2-17, 49:1:2-17, 49.5:1:2-17, 50:1:2-17, 50.5:1:2-17, 51:1:2-17, 51.5:1:2-17, 52:1:2-17, 52.5:1:2-17, 53:1:2-17, 53.5:1:2-17, 54:1:2-17, 54.5:1:2-17, 55:1:2-17, 55.5:1:2-17, 56:1:2-17, 56.5:1:2-17, 57:1:2-17, 57.5:1:2-17, 58:1:2-17, 58.5:1:2-17, 59:1:2-17, 59.5:1:2-17, 60:1:2-17, 60.5:1:2-17, 61:1:2-17, 61.5:1:2-17, 62:1:2-17, 62.5:1:2-17, 63:1:2-17, 63.5:1:2-17, 64:1:2-17, 64.5:1:2-17, 65:1:2-17, 65.5:1:2-17, 66:1:2-17, 66.5:1:2-17, 67:1:2-17, 67.5:1:2-17, 68:1:2-17, 68.5:1:2-17, 69:1:2-17, 69.5:1:2-17, 70:1:2-17, 70.5:1:2-17, 71:1:2-17, 71.5:1:2-17, 72:1:2-17, 72.5:1:2-17, 73:1:2-17, 73.5:1:2-17, 74:1:2-17, 74.5:1:2-17, 75:1:2-17, 75.5:1:2-17, 76:1:2-17, 76.5:1:2-17, 77:1:2-17, 77.5:1:2-17, 78:1:2-17, 78.5:1:2-17, 79:1:2-17, 79.5:1:2-17, 80:1:2-17, 80.5:1:2-17, 81:1:2-17, 81.5:1:2-17, 82:1:2-17, 82.5:1:2-17, 83:1:2-17, 83.5:1:2-17, 84:1:2-17, 84.5:1:2-17, or 85:1:2-17; alternatively, the ratio may be 30-85:1:2, 30-85:1:2.5, 30-85:1:3, 30-85:1:3.5, 30-85:1:4, 30-85:1:4.5, 30-85:1:5, 30-85:1:5.5, 30-85:1:6, 30-85:1:6.5, 30-85:1:7, 30-85:1:7.5, 30-85:1:8, 30-85:1:8.5, 30-85:1:9, 30-85:1:9.5, 30-85:1:10, 30-85:1:10.5, 30-85:1:11, 30-85:1:11.5, 30-85:1:12, 30-85:1:12.5, 30-85:1:13, 30-85:1:13.5, 30-85:1:14, 30-85:1:14.5, 30-85:1:15, 30-85:1:15.5, 30-85:1:16, 30-85:1:16.5, or 30-85:1:17. Preferably, the solution, the oil, and the surfactant are present in the o/w microemulsion in a weight ratio from about 40-80:1:3-8. In one example, the ratio is about 43.5:1:5.5; in another example, the ratio is about 53:1:6; in still another example, the ratio is about 64.5:1:6.5; in yet another example, the ratio is about 78:1:7.5; in still yet another example, the ratio is about 68:1:3.5; in still yet another example, the ratio is about 62:1:3.5; in still yet another example, the ratio is about 66:1:5; in still yet another example, the ratio is about 60.5:1:5.

The o/w microemulsion of the present disclosure is comprised of droplets having an average diameter of less than about 300 nm, such as in the range of 5-250 nm; preferably, in the range of 20-200 nm; more preferably, in the range of 30-150 nm. In one example, the o/w microemulsion is comprised of droplets of about 35-60 nm in diameter. In another example, the o/w microemulsion is comprised of droplets of about 45-90 nm in diameter. In yet another example, the o/w microemulsion is comprised of droplets of about 40-100 nm in diameter.

According to some embodiments of the present disclosure, the API of the present pharmaceutical composition has low water solubility or in general, substantially water immiscible. Exemplary API suitable for used in the present disclosure may be an antiepileptic, an analgesic, an antipsychotic, an anxiolytic, a tranquilizer, an anti-depressant, an incitant, an anti-dementia drug, an anti-parkinson drug, an anesthetic, a parasympathomimetic, a drug used in addictive disorders, a cardiac stimulant, an antiarrhythmic, an antihypertensive, a diuretic, a beta blocking agent, a calcium channel blocker, an agent acting on the renin-angiotensin system a lipid-modifying agent, an antithrombotic agent, an antihemorrhagic, an antiemtic, a propulsive, an antidiarrheal, an antiobesity preparation, a drug for diabetes, an enzyme, a vitamin, an antihistamine, a drug for obstructive airway diseases, an immunostimulant, an immunosuppressant, an anti-inflammatory drug, an antirheumatic drug, a muscle relaxant, an antiglaucoma preparation, an miotic, an antifungal, a drug for wounds and ulcers, an antibiotic, a disinfectant, an anti-acne preparation, an anti-cancer drug, an antiinfective, an antibacterial, an antimycobacterial, an antimycotic, an antiviral agent, an anthelmintic, an antinematodal agent, an antiprotozoal, a hormone preparation, or an antidote. In one specific example, the API of the present pharmaceutical composition is an anti-cancer drug.

Exemplary anti-cancer drug suitable for used as the API of the present pharmaceutical composition includes actinomycin, altretamine, aminoglutethimide, amsacrin, anastrozole, anthracycline, antiestrogen, asparaginase, bexaroten, bleomycin, bortezomib, buselerin, busulfan, camptothecin, capecitabine, carboplatin, carmustine, chlorambucil, cisplatin, cladribine, clofarabine, curcumin, cyclophosphamide, cytarabine, cytosinarabinoside, dacarbazine, dactinomycin, daunorubicin, dexamethasone, docetaxel, doxorubicin, epirubicin, estramustine, estrone, estradiol, estriol, etoposide, exemestane, fludarabine, fluorouracil, formestane, foxuridine, gemcitabine, glucocorticoid, hydroxyurea, idarubicin, indirubin, ifosfamide, imatinib, irinotecan, ixabepilone, letrozole, leuprolide, lomustine, mechlorethamine, melphalan, mercaptopurine, methotrexate, methylprednisolone, miltefosin, mitomycin, mitoxantrone, nimustine, nintedanib, oxaliplatin, paclitaxel, pentostatin, pemetrexed, plicamycin, prednisone, procarbazine, progesterone, streptozotocin, tamoxifen, temozolomide, teniposide, testolactone, testosterone, thiotepa, thioguanine, topotecan, treosulfan, tretinoin, triptorelin, trofosfamide, vinblastine, vincristine, vindesine, and vinorelbine. Preferably, the anti-cancer drug for used in the present disclosure is altretamine, aminoglutethimide, amsacrin, anastrozole, anthracycline, antiestrogen, bexaroten, bortezomib, busulfan, camptothecin, capecitabine, carboplatin, chlorambucil, cisplatin, cladribine, clofarabine, curcumin, dacarbazine, dactinomycin, dexamethasone, docetaxel, doxorubicin, estrone, estradiol, estriol, etoposide, exemestane, fludarabine, fluorouracil, formestane, foxuridine, gemcitabine, glucocorticoid, idarubicin, indirubin, imatinib, irinotecan, ixabepilone, letrozole, leuprolide, lomustine, mechlorethamine, melphalan, mercaptopurine, methotrexate, mitomycin, mitoxantrone, nintedanib, oxaliplatin, paclitaxel, plicamycin, prednisone, procarbazine, progesterone, tamoxifen, temozolomide, teniposide, testolactone, testosterone, thioguanine, treosulfan, tretinoin, triptorelin, trofosfamide, vinblastine, or vindesine. Nevertheless, the API of the present pharmaceutical composition is not limited thereto. In one particular example, the API of the present pharmaceutical composition is indirubin. In another example, the API of the present pharmaceutical composition is curcumin.

Basically, for the preparation of the present pharmaceutical composition, the water immiscible API is dissolved in the oil based on the solubility of the API in oil. Alternatively, the API and the oil may be formulated in a ratio of $1\times10^{-4}$:1-10:1 (w/v), for example, the ratio of the API and the oil is $1\times10^{-4}$:1, $2\times10^{-4}$:1, $3\times10^{-4}$:1, $4\times10^{-4}$:1, $5\times10^{-4}$:1, $6\times10^{-4}$:1, $7\times10^{-4}$:1, $8\times10^{-4}$:1, $9\times10^{-4}$:1, $1\times10^{-3}$:1, $2\times10^{-3}$:1, $3\times10^{-3}$:1, $4\times10^{-3}$:1, $5\times10^{-3}$:1, $6\times10^{-3}$:1, $7\times10^{-3}$:1, $8\times10^{-3}$:1, $9\times10^{-3}$:1, 0.01:1, 0.02:1, 0.03:1, 0.04:1, 0.05:1, 0.06:1, 0.07:1, 0.08:1, 0.09:1, 0.1:1, 0.15:1, 0.2:1, 0.25:1, 0.3:1, 0.35:1, 0.4:1, 0.45:1, 0.5:1, 0.55:1, 0.6:1, 0.65:1, 0.7:1, 0.75:1, 0.8:1, 0.85:1, 0.9:1, 0.95:1, 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (w/v). In one specific example, the ratio of the API and the oil is $1\times10^{-3}$:1 (w/v) (i.e., 1 mg API is dissolved in 1 ml oil). In another specific example, the ratio of the API and the oil is $3\times10^{-4}$:1 (w/v) (i.e., 0.3 mg API is dissolved in 1 ml oil).

In general, the API is present in the pharmaceutical composition at a level of about 0.01% to 99% by weight, based on the total weight of the pharmaceutical composition. In some embodiments, the API is present at a level of at least 0.1% by weight, based on the total weight of the pharmaceutical composition. In certain embodiments, the API is present at a level of at least 1% by weight, based on the total weight of the pharmaceutical composition. In other embodiments, the API is present at a level of at least 5% by weight, based on the total weight of the pharmaceutical composition. In still other embodiments, the API is present at a level of at least 10% by weight, based on the total weight of the pharmaceutical composition. In still yet other embodiments, the API is present at a level of at least 25% by weight, based on the total weight of the pharmaceutical composition.

2. Method of Use

The present invention encompasses a method for the treatment of a subject having a cancer. The method comprises the step of administering a therapeutically effective amount of the pharmaceutical composition of the present disclosure to the subject, in order to suppress the growth of the cancer.

In the present methods, the present pharmaceutical composition may be administered via a suitable route as known to those skilled in the art, including oral, intracranial, intraspinal, intrathecal, intramedullar, intracerebral, intracerebroventricular, intravenous, intraarterial, intracardial, intracutaneous, subcutaneous, transdermal, intraperitoneal, or intramuscular route. In general, the most appropriate route of administration will depend upon a variety of factors including the nature of the pharmaceutical composition (e.g., its stability in circulation), and/or the condition of the subject (e.g., whether the subject is able to tolerate intraperitoneal or intravenous administration).

It will be understood that the exact amount of the present pharmaceutical composition to achieve a medical efficacy will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the species, age, body weight, general health, sex, and diet of the subject; severity of the side effects or disorder; the time of administration, route of administration, and rate of excretion of the specific active ingredient employed; the duration of the treatment; and like factors well known in the medical arts.

A therapeutically effective amount may be included in a single dose (e.g., single intravenous injection dose) or multiple doses (e.g., multiple intravenous injection doses). In certain embodiments, when multiple doses are administered to a subject, the frequency of administering the multiple doses to the subject is three doses a day, two doses a day, one dose a day, one dose every other day, one dose every third day, one dose every week, one dose every other week, one dose monthly or one dose every other month. In certain embodiments, the frequency of administering the multiple doses to the subject is one dose per day. In certain embodiments, the frequency of administering the multiple doses to the subject is one dose every other day (or three times per week). In certain embodiments, the frequency of administering the multiple doses to the subject is one dose every third day (or twice per week). In certain embodiments, when multiple doses are administered to a subject, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject. In certain embodiments, the duration between the first dose and last dose of the multiple doses is three months, six months, or one year. In certain embodiments, the duration between the first dose and last dose of the multiple doses is the lifetime of the subject. In a specific embodiment, the duration between the first dose and last dose of the multiple doses is three weeks.

The method may further comprise administering to the subject one or more additional therapeutics prior to, concurrently with or after administering the present pharmaceutical composition to the subject. The additional therapeutic(s) is/are useful in preventing and/or treating cancers, such as a surgery, a radiotherapy, a chemotherapy, an immunotherapy, a hormone therapy, a targeted therapy, a thermal therapy, or a combined therapy thereof. In certain embodiments, combined use of the present pharmaceutical composition and the additional therapeutics exhibits a synergistic effect on the treatment of cancers. When such combined therapeutics is applied during the term of the present treatment, different therapies or therapeutics may be administered to the cancer patients at different time intervals via different routes, according to the dose and/or on the time schedule determined for that therapies or therapeutics.

In the present disclosure, the cancer treatable by the present methods include, but are not limited to, bladder cancer, biliary cancer, bone cancer, brain tumor, breast cancer, cervical cancer, colorectal cancer, dysgerminoma, esophageal cancer, epidermal cancer, gastric cancer, gastrointestinal stromal tumor (GIST), glioma, non-Hodgkin's lymphoma, head and neck cancer, intestinal cancer, Kaposi's sarcoma, liver cancer, lung cancer, lymphoma, lymphoid leukemia, melanoma, myeloid leukemia, nasopharyngeal cancer, oral cancer, ovary cancer, pancreatic cancer, prostate cancer, retinoblastoma, renal cell carcinoma, sarcoma, seminoma, skin cancer, spleen cancer, squamous cell carcinoma, teratoma, teratocarcinoma, thyroid cancer, or thyroid follicular cancer. According to one preferred embodiment, the cancer treatable by the present pharmaceutical composition is lung cancer. The cancer may be an in situ cancer or a metastatic cancer.

According to some embodiments of the present disclosure, the subject treatable by the present pharmaceutical composition is a mammal. In one example, the subject treatable by the present pharmaceutical composition is a human. In another example, the subject treatable by the present pharmaceutical composition is a mouse.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

1. Cell Culture

Human lung cancer cell line A549 (ATCC® CCL-185™) and human foreskin fibroblasts Hs68 (ATCC® CRL-1635™) was grown in the base medium of Dulbecco's Modified Eagle's Medium (DMEM) (Gibco, U.S.A.), supplemented with 10% fetal bovine serum (FBS), 4 mM L-glutamine, 1.5 g/L sodium bicarbonate (Sigma-Aldrich), and 4.5 g/L glucose. Human embryonic kidney cell line HEK-293 (ATCC® CRL-1573™) was grown in the base medium of DMEM/F12K (Gibco, U.S.A.), supplemented with 10% FBS, 2 mM L-glutamine, 1.5 g/L sodium bicarbonate (Sigma-Aldrich), and 100 U/ml penicillin and 100 µg/ml streptomycin (Gibco, U.S.A.). Cells were grown at 37° C. with a humidified atmosphere of 5% $CO_2$ in air.

2. Particle Size Analysis

The present pharmaceutical compositions were analyzed using a particle size analyzer (NanoBrook 90Plus, Brookhaven Instruments Corporation, U.S.A.) with the parameters listed in Table 1.

TABLE 1

| Parameters set for the particle size analysis | | | |
|---|---|---|---|
| Runs | 3 | Batch # | 0 |
| Temp. | 25.0 | Run Duration | |
| Liquid | Water | Minutes | 0 |
| Viscosity | 1.330 | Second | 30 |
| Ref. Index | 0.890 | Refractive Index of Particles | |
| Angle | 90.00 | Real | 1.590 |
| Wavelength | 658.0 | Imaginary | 0.000 |
| Dust Cutoff | 30.00 | ■ Uniform Spheres ☐ Thin Shells | |

3. Cell Viability Assay

A549 or HEK-293 cells were plated into a 96-well microplate, and incubated for 24 hrs at 37° C. The present pharmaceutical compositions were filtered with a 0.22 µm filter, and then added into the cultures. The cultures were incubated for another 24 hrs at 37° C. Next, the MTT reagent (3-(4,5-dimethylthiazol-2-yl)-2,5-diphenyltetrazolium bromide) (Sigma-Aldrich, U.S.A.) was added into the cultures, and incubated for 3 hrs at 37° C. After that, the supernatant of the cultures was discarded, and dimethyl sulfoxide (DMSO) (100 µL/well) was added into the cultures and incubated for 30 mins 37° C. The absorbance was measured with a microplate reader (CLARIOstar®, BMG Labtech, Germany).

4. Dilution Analysis

The present pharmaceutical compositions were diluted 30, 60, 120 and 240 times with PBS, and incubated for 0, 1, 3, 6, and 24 hrs at room temperature (RT). The absorbance of 530 nm was measured with a microplate reader (CLARIOstar®, BMG Labtech, Germany).

Example 1 Preparation and Characterization of the Present Pharmaceutical Compositions 1.1 Preparation of the Present Pharmaceutical Compositions To start with, indirubin (1 mg) or curcumin (0.33 mg) was dissolved in olive oil (1 ml). For the preparation of the o/w microemulsion, lecithin was first mixed with distilled water (or DI water) by vortex, and then TWEEN 80 (herein after abbreviated as "Tw80") was added and the thus resulted mixture was mixed by vortex. Next, the oil containing indirubin was added into the o/w microemulsion and thoroughly mixed by vortex; the entire mixture was sonicated for 30 mins at 60° C., and sat still for 10 mins. The sonication step was repeated 3 times to give the desired formulation.

A total of 8 formulations for indirubin were produced, in which the A series (formulations A-1 to A-4) and the B series (formulations B-1 to B-4) differed in the amount of Tw80 used in the formulation. Also, a total of 4 formulations for curcumin were produced (C series; formulations C-1 to C-4). The list of the components and their respective proportions are summarized in Tables 2 and 3.

TABLE 2

| Component list of the formulation | | | | | |
|---|---|---|---|---|---|
| Formulation No. | Total (g) | DI water (g) | Lecithin (g) | Tw80 (g) | Oil (containing indirubin or curcumin) (g) |
| A-1 | 9.000 | 7.474 | 0.422 | 1.000 | 0.104 |
| A-2 | 9.000 | 7.369 | 0.507 | 1.000 | 0.125 |
| A-3 | 9.000 | 7.242 | 0.608 | 1.000 | 0.149 |
| A-4 | 9.000 | 7.091 | 0.730 | 1.000 | 0.179 |
| B-1 | 9.000 | 8.115 | 0.282 | 0.500 | 0.104 |
| B-2 | 9.000 | 8.038 | 0.338 | 0.500 | 0.125 |
| B-3 | 9.000 | 7.945 | 0.405 | 0.500 | 0.149 |
| B-4 | 9.000 | 7.834 | 0.486 | 0.500 | 0.179 |
| C-1 | 3.000 | 2.812 | 0.135 | 0.012 | 0.042 |
| C-2 | 3.000 | 2.797 | 0.146 | 0.012 | 0.045 |
| C-3 | 3.000 | 2.750 | 0.203 | 0.006 | 0.042 |
| C-4 | 3.000 | 2.730 | 0.220 | 0.006 | 0.045 |

TABLE 3

| The proportion of each component in the formulations of Table 2 | | | | |
|---|---|---|---|---|
| Formulation No. | DI water/ Total | Lecithin/ Total | Tw80/ Total | Oil (containing indirubin or curcumin)/Total |
| A-1 | 83% | 5% | 11% | 1% |
| A-2 | 82% | 6% | 11% | 1% |
| A-3 | 80% | 7% | 11% | 2% |
| A-4 | 79% | 8% | 11% | 2% |
| B-1 | 90% | 3% | 6% | 1% |
| B-2 | 89% | 4% | 6% | 1% |
| B-3 | 88% | 5% | 6% | 2% |
| B-4 | 87% | 5% | 6% | 2% |
| C-1 | 94% | 5% | 0.39% | 1% |
| C-2 | 93% | 5% | 0.39% | 2% |
| C-3 | 92% | 7% | 0.20% | 1% |
| C-4 | 91% | 7% | 0.20% | 2% |

1.2 Characterization of the Formulations of Example 1.1

1.2.1 Particle Size

The particle size of each formulation of Example 1.1 was analyzed. Results are depicted in FIGS. 1A-1C.

Figure 1B:
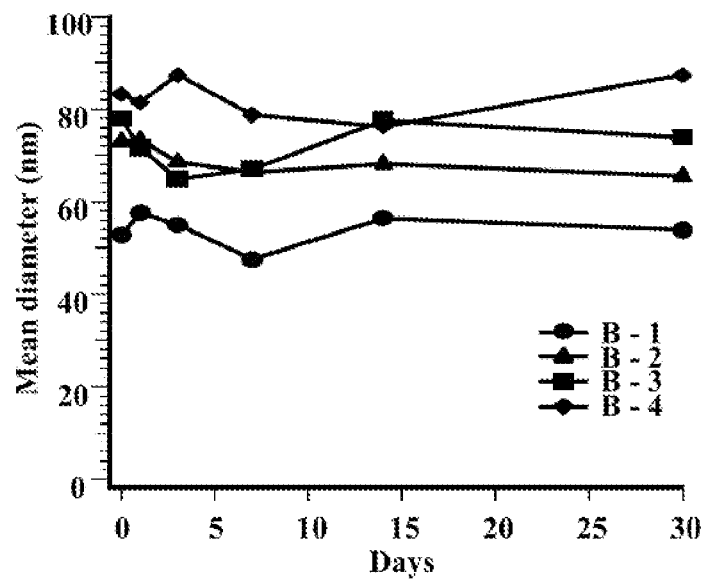
Figure 1C:
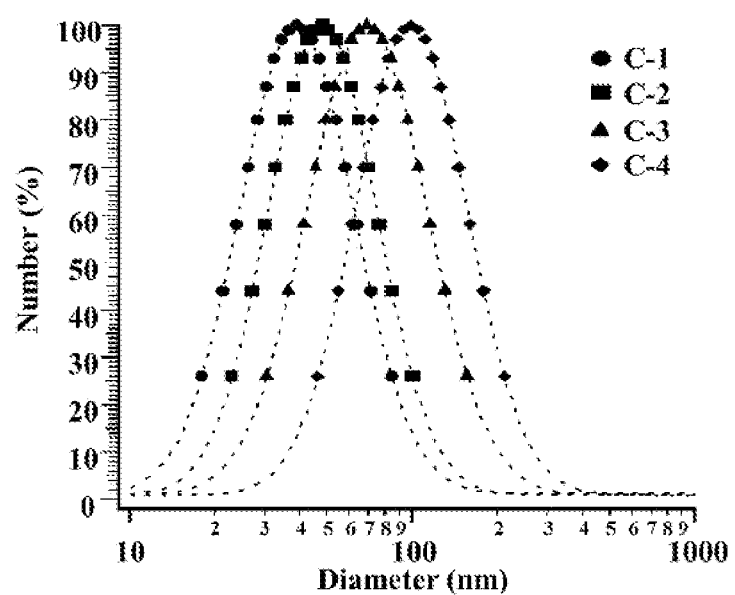

As illustrated in FIGS. 1A-1B, particles in the A-series formulation were relatively larger in size than those in the B-series, in which the particle size of A series falls in the range of 35 nm to 60 nm, whereas that of the B-series is in the range of 45 nm to 90 nm. Specifically, the particle sizes of formulations A-1, A-2, A-3, and A-4 were respectively 42-49 nm, 38-45 nm, 38-48 nm, and 47-59 nm; while the particle sizes of formulations B-1, B-2, B-3, and B-4 were respectively 47-58 nm, 65-77 nm, 63-78 nm, and 73-88 nm. Further, all formulations, including A-1 to A-4 and B-1 to B-4, remained stable for at least 1 month after filtered with a 0.22 µm filter.

Nonetheless, particle size distribution in the C-series formulations were more diversified; majority of the particle size of the C series fell in the range of 28 nm to 135 nm, whereas the particle size of the C series may range from 18 nm to 212 nm. Specifically, the particle size of formulations C-1, C-2, C-3, and C-4 were 18-85 nm, 23-100 nm, 31-156 nm, and 46-212 nm respectively; majority of the particle size of formulations C-1, C-2, C-3, and C-4 were 28-54 nm, 36-65 nm, 49-97 nm, and 73-135 nm respectively (FIG. 1C).

Figure 2A:
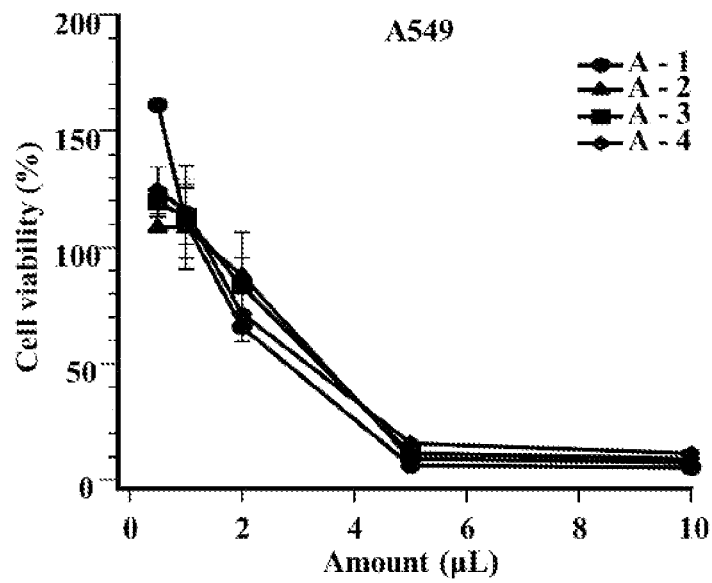
FIGS. 2A and 2B depict the percentage of cell viability of human lung cancer A549 cells (FIG. 2A) and human embryonic kidney HEK-293 cells (FIG. 2B) treated with the specified formulations respectively.
Figure 2B:
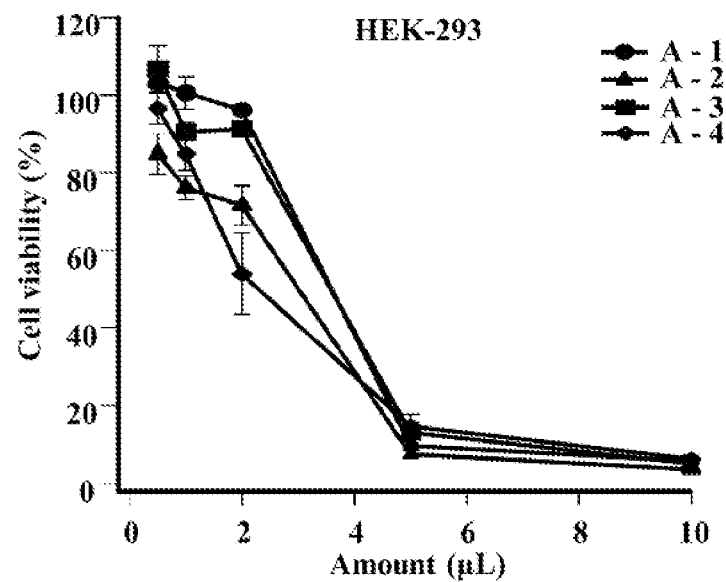

1.2.2 Effects of the Formulations of Example 1.1 on Cancerous or Non-Cancerous Cells The effect of the formulations of Example 1.1 on cancerous or non-cancerous cells was evaluated in this example. The results of FIG. 2 indicated that the A series formulations (A-1 to A-4) exhibited a cytotoxic effect on both cancerous cells (FIG. 2A) and non-cancerous cells (FIG. 2B) in a dose-dependent manner. Specifically, the overall cell viability of the cancerous A549 cells treated with A-1 to A-4 was about 6.4-15.8% when dose was 5 µL, and 5.4-11.3% when dose was doubled (10 µL) (FIG. 2A). The overall cell viability of the non-cancerous HEK-293 cells treated with A-1 to A-4 was about 7.53-14.7% when dose was 5 µL, and 3.6-6.22% when dose was doubled (10 µL) (FIG. 2B).

Figure 2C:
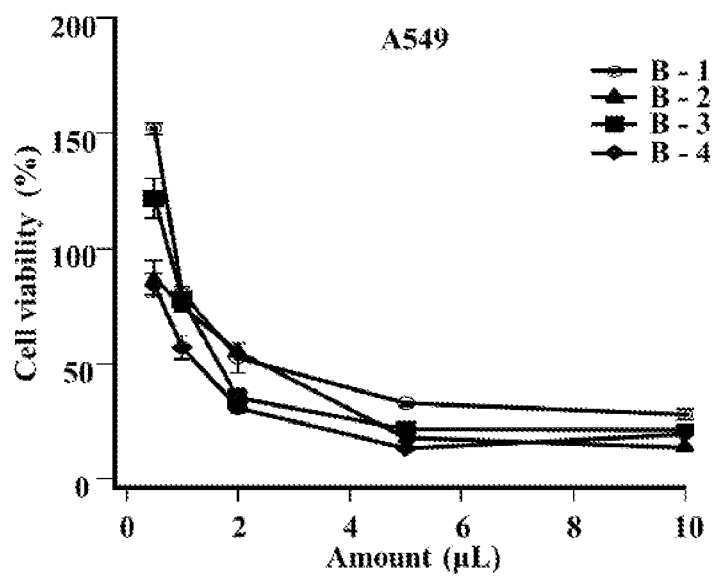
FIGS. 2C and 2D depict the percentage of cell viability of A549 cells (FIG. 2C) and HEK-293 cells (FIG. 2D) treated with the specified formulations respectively.
Figure 2D:
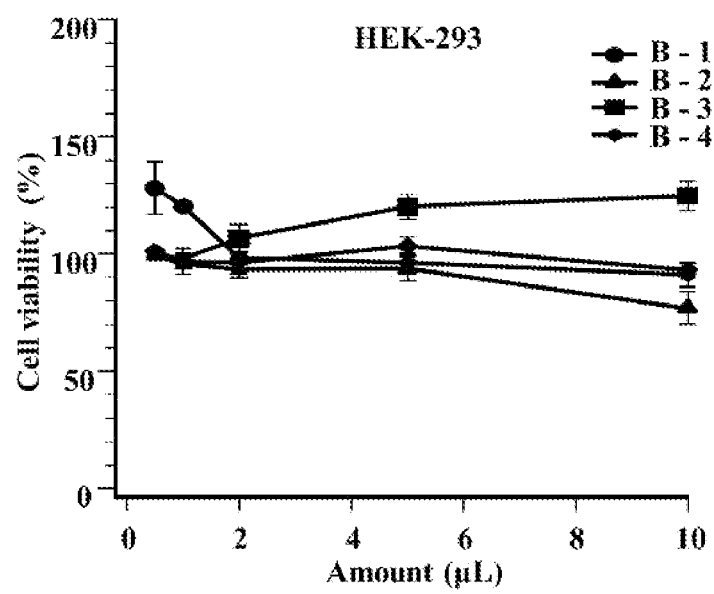

In contrast, B series formulations (B-1 to B-4) dose-dependently inhibited the viability of cancerous cells without affecting the viability of non-cancerous cells (FIGS. 2C and 2D). The overall cell viability of the cancerous A549 cells treated with B-1 to B-4 remained low; it was about 13.3-33.0% when dose was 5 µL, and 13.7-28.1% when dose was 10 µL (FIG. 2C). The overall cell viability of the non-cancerous HEK-293 cells treated with B-1 to B-4 was about 93.7-120.2% when dose was 5 µL, and 77.3-124.7% when dose was 10 µL (FIG. 2D).

1.2.3 Pair-Wise Comparison Between Formulations of Example 1.1 on their Cytotoxic Effects Towards Cancerous and Non-Cancerous Cells In this example, pair-wise comparison between the cytotoxicity of the formulations of Example 1.1 towards cancerous A549 cells and non-cancerous HEK-293 cells were performed, and results are depicted in FIGS. 3-6.

Figure 3:
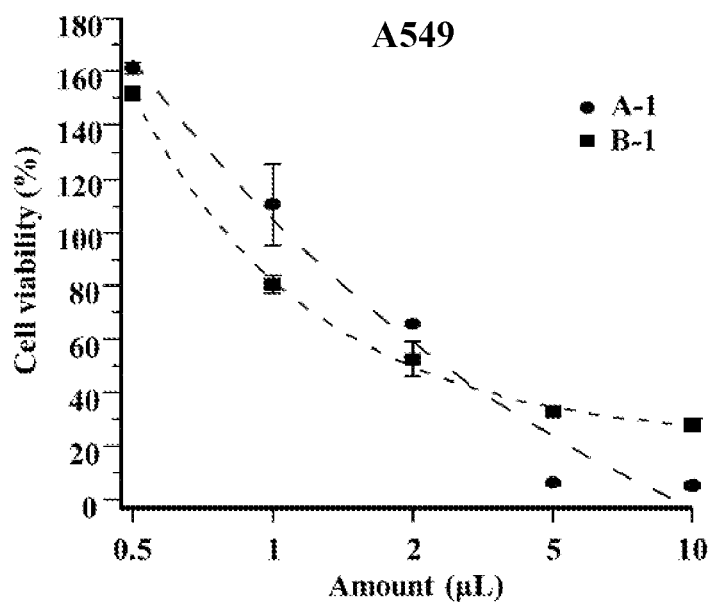
FIG. 3 depicts the percentage of cell viability in accordance with one embodiment of the present disclosure. Panel (A): A549 cells treated with formulation A-1 or B-1. Panel (B): HEK-293 cell treated with formulation A-1 or B-1.
Figure 3:
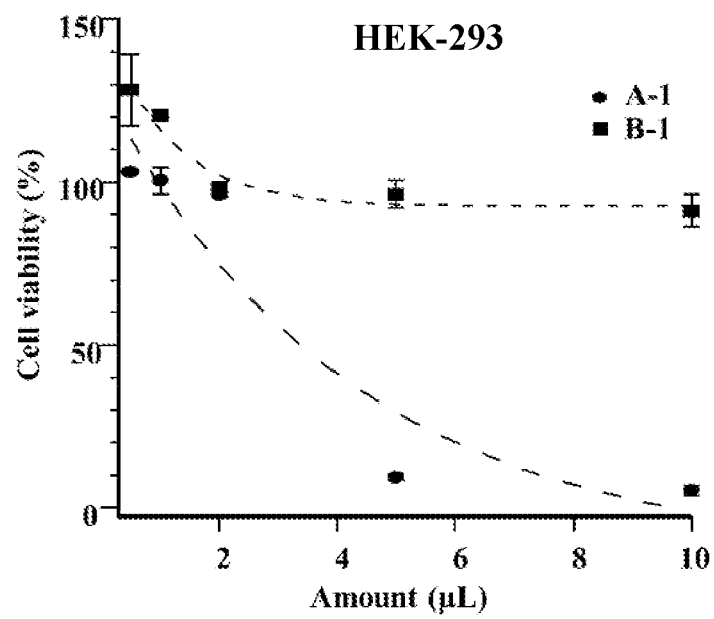
Figure 4:
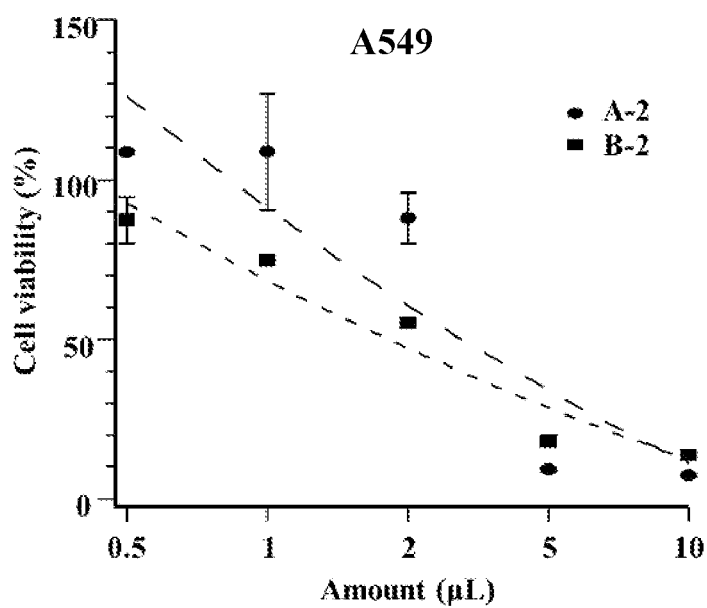
FIG. 4 depicts the percentage of cell viability in accordance with one embodiment of the present disclosure. Panel (A): A549 cells treated with formulation A-2 or B-2. Panel (B): HEK-293 cells treated with formulation A-2 or B-2.
Figure 4:
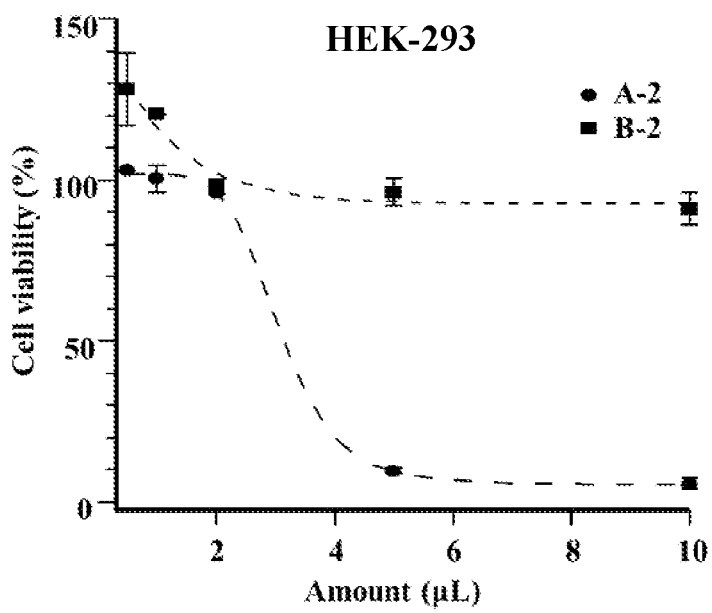
Figure 5:
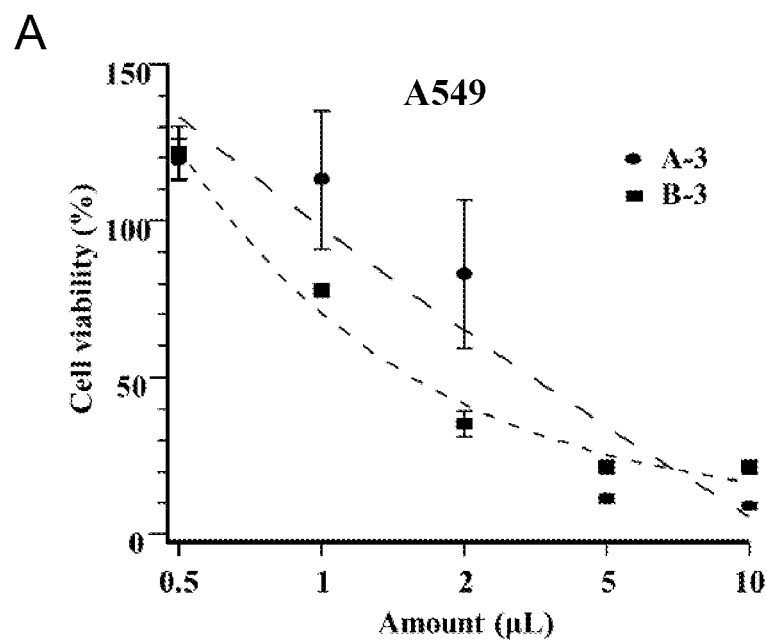
FIG. 5 depicts the percentage of cell viability in accordance with one embodiment of the present disclosure. Panel (A): A549 cells treated with formulation A-3 or B-3. Panel (B) HEK-293 cells treated with formulation A-3 and B-3.
Figure 5:
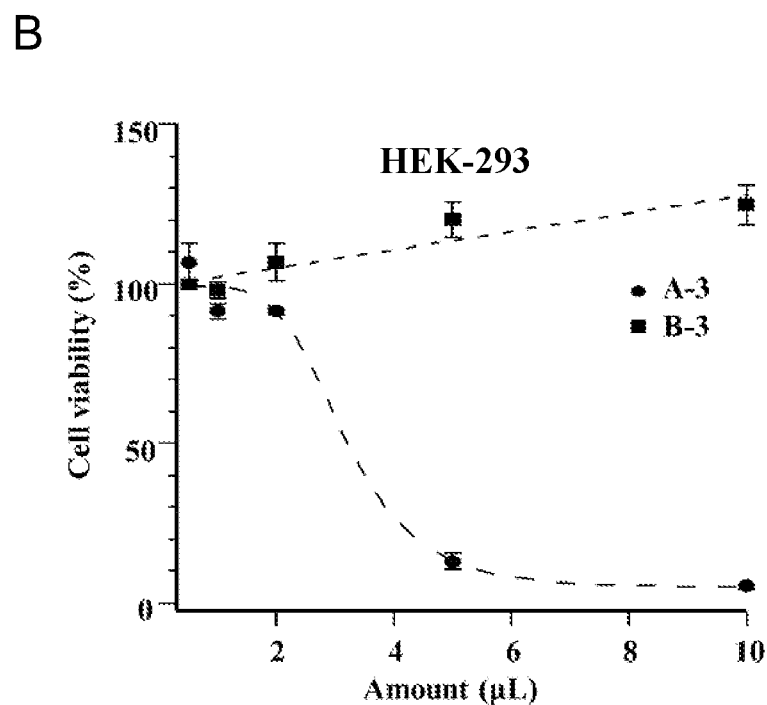
Figure 6:
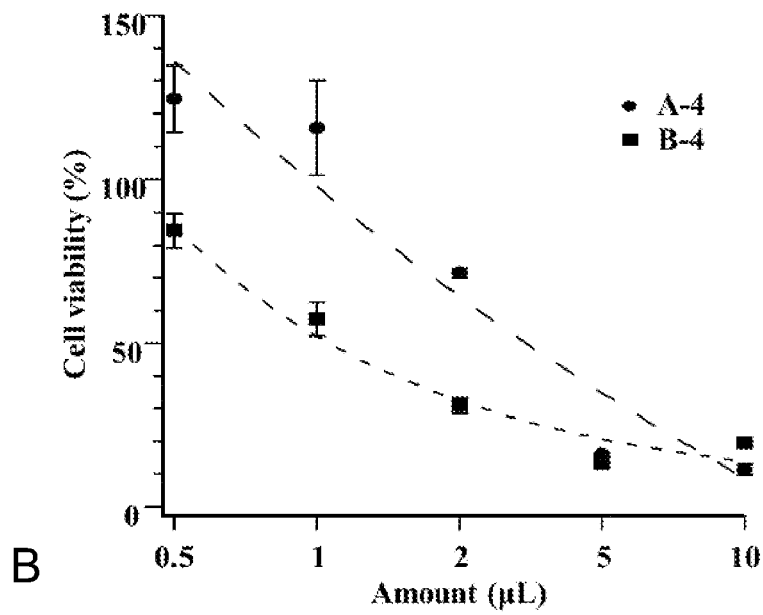
FIG. 6 depicts the percentage of cell viability in accordance with one embodiment of the present disclosure. Panel (A): A549 cells treated with formulation A-4 or B-4. Panel (B): HEK-293 cells treated with formulation A-4 and B-4.
Figure 6:
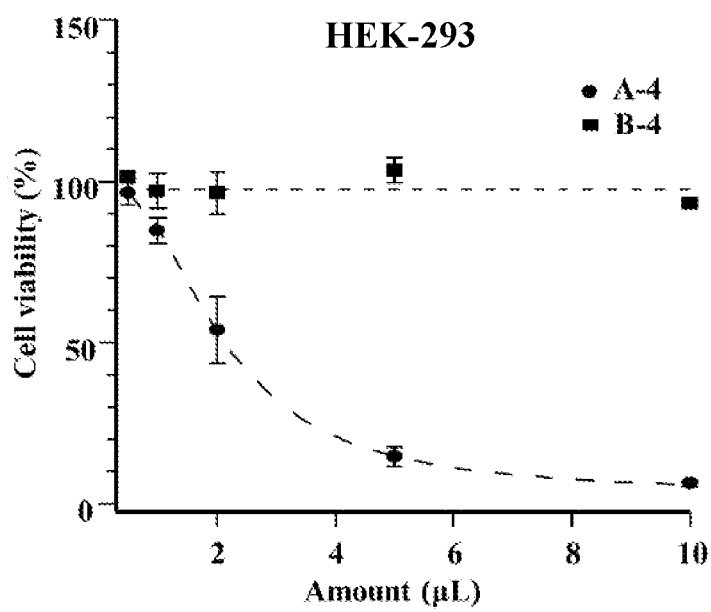
Figure 7A:
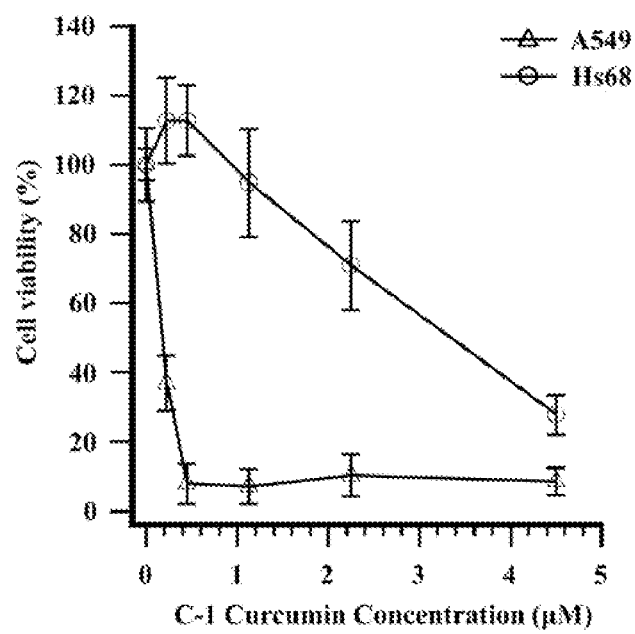
FIGS. 7A-7D depict the percentage of cell viability in accordance with one embodiment of the present disclosure. A549 or Hs68 cells were treated with formulation C-1 (FIG. 7A), C-2 (FIG. 7B), C-3 (FIG. 7C), or C-4 (FIG. 7D) respectively.
Figure 7B:
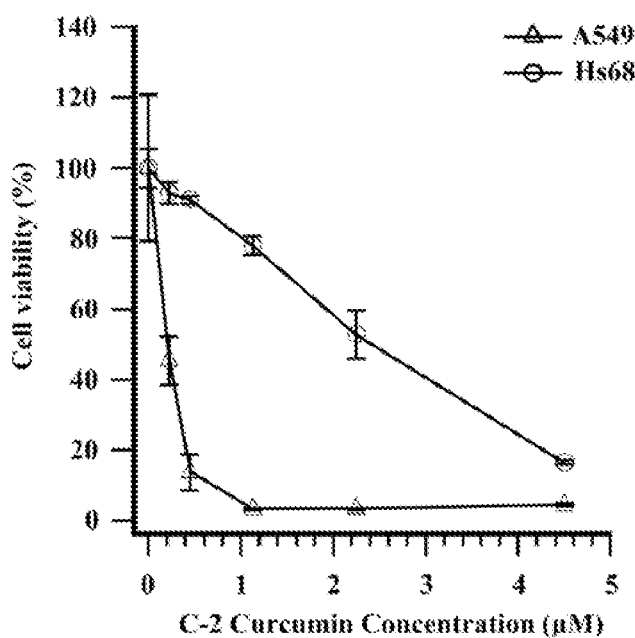
Figure 7C:
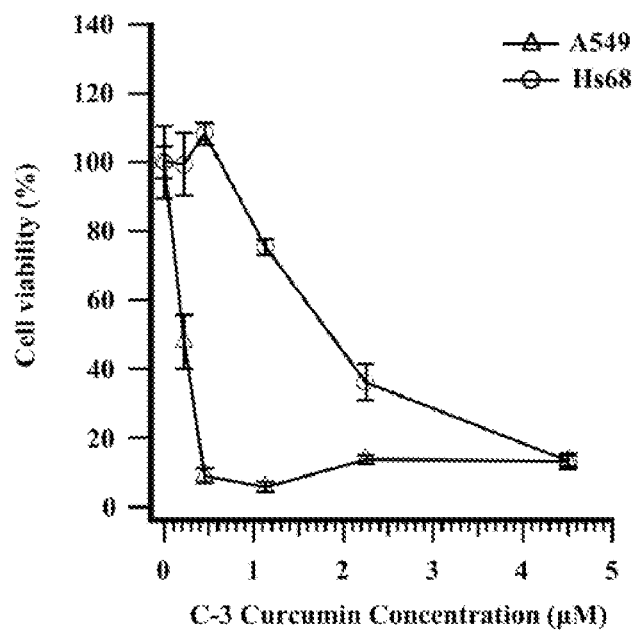
Figure 7D:
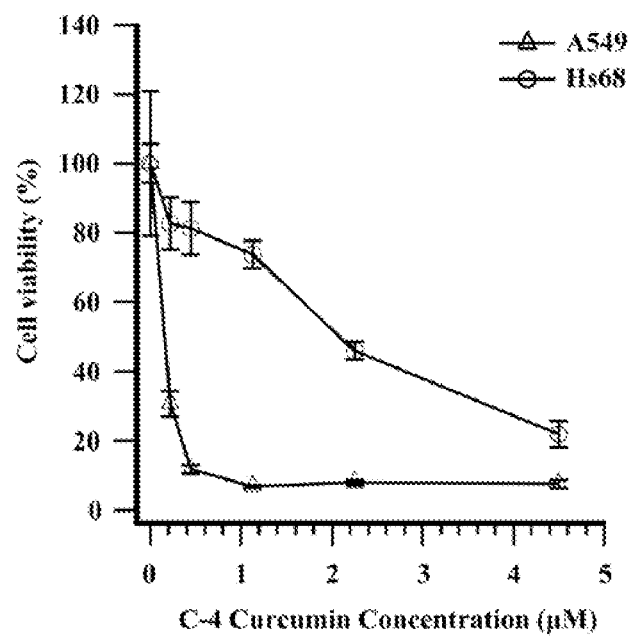

As illustrated in FIG. 3, both A-1 and B-1 exhibited cytotoxic effects on the cancerous A549 cells in a dose-dependent manner, specifically, in low dose (i.e., 0.5, 1, and 2 µL), the cell viability of A-1 formulation was higher than that of B-1 formulation; by contrast, in high dose (i.e., 5, and 10 µL), the cell viability of B-1 formulation was higher than that of A-1 (FIG. 3, panel (A)). However, in non-cancerous HEK-293 cells, only A-1, but not B-1 formulation, exhibited cell-killing effect in high dose (FIG. 3, panel (B)). Surprisingly, B-1 formulation did not result in any significant cell death, either in low dose or in high dose. Similar observations were found in pair-wise comparison between formulation pairs of A-2 and B-2, A-3 and B-3, as well as the pairs of A4 and B4 (see FIGS. 4 to 6).

The effects of C series formulations on the cytotoxicity of both A549 and Hs68 (skin fibroblasts, as a non-cancerous cell control) cells were also determined, and the results were illustrated in FIGS. 7A to 7D. As provided in FIG. 7A, C-1 formulation caused prominent cancerous A549 cells death in low concentration as less than 1 µM, whereas Hs68 cells did not exhibit remarkable cell death until the concentration of curcumin within formulation C-1 reached 2 µM Similar observations were revealed in formulation C-2, C-3, and C-4 in treating both A549 and Hs68 cells (see FIGS. 7B to 7D).

Taken together, the data in this example confirmed that although both A and B series formulations possessed cancer-killing effects, yet the B-series formulations were preferred choices as they exhibited selective killing effects, in which non-cancerous cells or normal tissues were not damaged while cancerous cells were destroyed.

1.2.4 Stability of the Present Pharmaceutical Compositions

Based on the findings in Example 1.2.3, formulations B-1 and B-4, which exhibited less cytotoxic effects toward non-cancerous cells, were selected for further investigation on their behaviors in conditions that mimic a live subject.

To this purpose, B-1 and B-4 were first diluted 30, 60, 120, and 240 times with PBS, and sat for 0, 1, 3, 6, and 24 hrs at room temperature before subjecting to absorbance measurement. Results are summarized in Table 4.

TABLE 4

Absorbance of B-1 and B-4 over time

| Dilution | Time (hr) | | | | |
|---|---|---|---|---|---|
| | 0 | 1 | 3 | 6 | 24 |
| B-1 | | | | | |
| 1× | 0.287 ± 0.002 | 0.284 ± 0.005 | 0.286 ± 0.007 | 0.283 ± 0.004 | 0.277 ± 0.008 |
| 30× | 0.078 ± 0.021 | 0.071 ± 0.009 | 0.076 ± 0.015 | 0.083 ± 0.022 | 0.082 ± 0.013 |
| 60× | 0.051 ± 0.005 | 0.058 ± 0.012 | 0.054 ± 0.005 | 0.055 ± 0.006 | 0.059 ± 0.003 |
| 120× | 0.039 ± 0.002 | 0.039 ± 0.002 | 0.040 ± 0.003 | 0.041 ± 0.002 | 0.043 ± 0.003 |
| 240× | 0.038 ± 0.004 | 0.044 ± 0.008 | 0.041 ± 0.005 | 0.044 ± 0.007 | 0.046 ± 0.008 |
| PBS | 0.033 ± 0.001 | 0.031 ± 0.001 | 0.032 ± 0.002 | 0.033 ± 0.003 | 0.035 ± 0.006 |
| B-4 | | | | | |
| 1× | 0.348 ± 0.011 | 0.344 ± 0.008 | 0.342 ± 0.008 | 0.342 ± 0.009 | 0.336 ± 0.011 |
| 30× | 0.083 ± 0.004 | 0.085 ± 0.003 | 0.085 ± 0.001 | 0.085 ± 0.002 | 0.092 ± 0.004 |

TABLE 4-continued

Absorbance of B-1 and B-4 over time

| Dilution | Time (hr) | | | | |
|---|---|---|---|---|---|
| | 0 | 1 | 3 | 6 | 24 |
| 60× | 0.056 ± 0.006 | 0.054 ± 0.003 | 0.054 ± 0.002 | 0.057 ± 0.006 | 0.057 ± 0.003 |
| 120× | 0.063 ± 0.022 | 0.061 ± 0.022 | 0.063 ± 0.022 | 0.070 ± 0.026 | 0.066 ± 0.026 |
| 240× | 0.055 ± 0.014 | 0.049 ± 0.005 | 0.048 ± 0.005 | 0.049 ± 0.005 | 0.049 ± 0.005 |
| PBS | 0.033 ± 0.001 | 0.031 ± 0.001 | 0.032 ± 0.002 | 0.033 ± 0.003 | 0.035 ± 0.006 |

It was found that the absorbance of B-1 at 530 nm before dilution was about 0.283 (±0.004), and was respectively about 0.078 (±0.005), 0.055 (±0.003), 0.040 (±0.001), and 0.043 (±0.003) after being diluted with PBS for 30, 60, 120, and 240 folds (see Table 4). The absorbance of PBS was about 0.033 (±0.003). The overall changes in the absorbance of B-1 at the respective dilutions were less than 7% in the period of 24 hrs.

Similar results were also observed for B-4 formulation, in which the absorbance of B-4 at 530 nm before dilution was about 0.342 (±0.004), and was respectively about 0.078 (±0.005), 0.086 (±0.003), 0.055 (±0.002), and 0.065 (±0.004) after being diluted with PBS for 30, 60, 120, and 240 folds (see Table 4). The overall changes in the absorbance of B-4 at the respective dilutions were less than 6.1% in the period of 24 hrs.

Another approach for assessing the stability of the B-1 or B-4 formulations over time was by monitoring the changes in the particle sizes. To this purpose, each formulation was diluted 30, 60, 120, or 240 times with PBS, and sat for 0, 1, 3, 6, and 24 hrs at room temperature before subjecting to particle size analysis. Results are provided in Table 5.

TABLE 5

Particle size of B-1 and B-4 over time

| Dilution | Time (hr) | | | | |
|---|---|---|---|---|---|
| | 0 | 1 | 3 | 6 | 24 |
| B-1 | | | | | |
| 1× | 59.7 | 53 | 63.5 | 61.9 | 55.8 |
| 30× | 30.1 | 27.7 | 36.5 | 42.4 | 29.6 |
| 60× | 29.8 | 33.2 | 30.9 | 35.3 | 46.8 |
| 120× | 31.5 | 36.8 | 40.7 | 46.6 | 29.3 |
| 240× | 33.6 | 29.1 | 21.3 | 27.1 | 20.3 |
| PBS | 36.7 | 44.4 | 30.7 | 30 | 34.1 |
| B-4 | | | | | |
| 1× | 84.6 | 81.8 | 82 | 87.3 | 70 |
| 30× | 30.6 | 33.5 | 27.6 | 38 | 38.2 |
| 60× | 36.2 | 30.8 | 37.1 | 29.9 | 37.2 |
| 120× | 31.4 | 35.1 | 42.2 | 44.3 | 34.7 |
| 240× | 35.8 | 41.5 | 41.2 | 42.7 | 38.7 |
| PBS | 36.7 | 44.4 | 30.7 | 30 | 34.1 |

It was found that the particle size of B-1 formulation was about 53-64 nm before dilution, and was respectively about 27-43 nm, 29-47 nm, 29-47 nm, and 20-34 nm after being diluted with PBS for 30, 60, 120, and 240 folds, and the particle size of PBS was about 30-45 nm (control) (see Table 5). The results indicated that, the particles of B-1 became smaller after dilution; however, the particle size remained relatively constant up to 24 hrs, suggesting that dilution did not affect the integrity of each particle of B-1.

Similar results were also seen in B-4. The particle size of B-4 formulation was about 70-88 nm before dilution, and was respectively about 30-39 nm, 29-38 nm, 31-45 nm, and 35-43 nm after being diluted with PBS for 30, 60, 120, and 240 folds, and the particle size of PBS was about 30-45 nm (control) (see Table 5). The results indicated that, the particles of B-4 became smaller after dilution; however, the particle size remained relatively constant up to 24 hrs, suggesting that dilution did not affect the integrity of each particle of B-4.

Taken together, the results in this example suggested that both B-1 and B-4 formulations would remain stable for at least 24 hrs after being administered into a subject.

In conclusion, results for Example 1 demonstrates that the present formulation, in which APIs with low water solubility are successfully incorporated into o/w micro-emulsion may achieve selective cell-killing effect on cancer cells, and the formulation remains stable for at least for 24 hrs in a physiological condition.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating lung cancer cells comprising administering to the lung cancer cells an effective amount of a pharmaceutical composition, wherein the pharmaceutical composition comprises an oil-in-water (o/w) microemulsion and indirubin or curcumin dissolved therein; wherein
   the o/w microemulsion comprises an aqueous solution, an oil, and a surfactant, which are respectively present in a ratio of about 40-80:1:3-8 by weight in the o/w microemulsion; and
   the o/w microemulsion is about 5-250 nm in diameter.

2. The method of claim 1, wherein the aqueous solution is water or a buffered solution.

3. The method of claim 1, wherein the oil is selected from the group consisting of almond oil, canola oil, castor oil, corn oil, cottonseed oil, olive oil, safflower oil, sesame oil, soybean oil, isopropyl myristate, isopropyl palmitate, isopropyl stearate, ethyl oleate, myristic alcohol, oleyl alcohol, myristic acid, oleyl acid, palmitic acid, triglycerides, diglycerides, monoglycerides, and a combination thereof.

4. The method of claim 1, wherein the surfactant is consisted of a first and a second emulsifiers in a ratio from about 0.1:1 to 50:1 by weight.

5. The method of claim 4, wherein the first emulsifier is selected from the group consisting of egg lecithin, glycerophosphocholine, hydrogenated phosphatidyl choline, hydrogenated phospholipids, hydrogenated soybean lecithin, phospholipids, sodium lauryl sulphate, soybean lecithin, and soybean lysolecithin.

6. The method of claim 4, wherein the second emulsifier is selected from the group consisting of caprylocaproyl polyoxylglyceride, lauroyl polyoxylglyceride, oleoyl polyoxylglyceride, pegylated hydroxystearate, pegylated stearate, polyoxyethylene castor oil, polyoxyethylene cetostearyl ether, polyoxyethylene cetyl stearyl ether, polyoxyethylene dioleate, polyoxyethylene glycol cetyl ether, polyethylene glycol stearyl ether, polyoxyethylene hydrogenated castor oil, polyoxyethylene isostearyl ether, polyethylene laurate, polyoxyethylene monocetyl ether, polyoxyethylene oleate, polyoxyethylene sorbitan, and sorbitan.

7. The method of claim 4, wherein the first and second emulsifiers are respectively soybean lecithin and polyoxyethylene sorbitan.

* * * * *